US008313956B2

(12) United States Patent
Bailey

(10) Patent No.: US 8,313,956 B2
(45) Date of Patent: Nov. 20, 2012

(54) APPARATUS AND ASSOCIATED METHODS

(75) Inventor: Marc James Ashton Bailey, Cambridge (GB)

(73) Assignee: Nokia Corporation, Espoo (FI)

( * ) Notice: Subject to any disclaimer, the term of this patent is extended or adjusted under 35 U.S.C. 154(b) by 389 days.

(21) Appl. No.: 12/720,598

(22) Filed: Mar. 9, 2010

(65) Prior Publication Data

US 2011/0223689 A1 Sep. 15, 2011

(51) Int. Cl.
*G01N 33/558* (2006.01)

(52) U.S. Cl. ........ 436/514; 436/518; 436/177; 436/178; 422/50; 422/420; 422/430; 422/68.1; 422/82.01
(58) Field of Classification Search .................. 436/514, 436/518, 177, 178; 422/50, 420, 430, 68.1, 422/82.01
See application file for complete search history.

(56) References Cited

U.S. PATENT DOCUMENTS

| | | | | |
|---|---|---|---|---|
| 6,602,719 | B1 * | 8/2003 | Carpenter | 436/518 |
| 6,663,833 | B1 * | 12/2003 | Stave et al. | 422/81 |
| 7,052,846 | B2 * | 5/2006 | Van Ness et al. | 435/6.12 |
| 7,309,723 | B2 * | 12/2007 | Porter et al. | 522/104 |
| 7,858,321 | B2 * | 12/2010 | Glezer et al. | 435/7.1 |
| 7,879,597 | B2 * | 2/2011 | Esfandiari | 435/287.2 |
| 2003/0119203 | A1 | 6/2003 | Wei et al. | 433/514 |
| 2003/0153094 | A1 | 8/2003 | Alocilja et al. | 436/516 |
| 2005/0136500 | A1 | 6/2005 | Yang et al. | 435/14 |
| 2010/0041049 | A1 * | 2/2010 | Smith et al. | 435/6 |

FOREIGN PATENT DOCUMENTS

| | | |
|---|---|---|
| EP | 0 291 194 | 11/1988 |
| WO | WO 2005/090987 A1 | 9/2005 |
| WO | WO 2009/024775 A1 | 2/2009 |

OTHER PUBLICATIONS

Majd, et al., "Applications of Biological Pores in Nanomedicine, Sensing, and Nanoelectronics", Current Opinion in Biotechnology, vol. 21, No. 4, (2010), (pp. 439-479).
Martinez, et al., "Highly Efficient Biocompatible Single Silicon Nanowire Electrodes with Functional Biological Pore Channels", Nano Letters vol. 9, No. 3, (2009), (pp. 1121-1126).
Misra, et al., "Bioelectronic Silicon Nanowire Devices Using Functional Membrane Proteins", vol. 106, No. 33, (2009), (pp. 13781-13784).

* cited by examiner

*Primary Examiner* — Melanie J Yu
(74) *Attorney, Agent, or Firm* — Harrington & Smith

(57) ABSTRACT

An apparatus for the selective release of a bound species based on the presence of an analyte, the apparatus comprising:

a first and second receptor species, the first receptor species linked with a bound species and configured to interact with an analyte to form a first intermediate complex, the bound species for causing increased porosity of a membrane of an in-contact analyte sensor apparatus to correspondingly increase exposure of a sensing element of the analyte sensor apparatus to allow for production of a detectable electrical signal which can be used to sense the presence of the analyte, the second receptor species for interacting with the first intermediate complex to form a second intermediate complex; and a cleaving species, the cleaving species configured to interact with the second intermediate complex to release the bound species for use in sensing the presence of the analyte.

23 Claims, 9 Drawing Sheets

APPARATUS AND ASSOCIATED METHODS

TECHNICAL FIELD

The present disclosure relates to the field of (e.g. nanowire) sensors, associated methods and apparatus, and in particular concerns an indirect sensing mechanism that couples analyte-receptor recognition to an increase in porosity of a membrane layer. One or more techniques described herein may or may not be suitable for the detection of different types of molecules in gases or aqueous fluids, or for health monitoring using portable electronic devices.

BACKGROUND

The detection of biological and chemical species is central to many areas of healthcare and the life sciences, ranging from uncovering and diagnosing disease to the discovery and screening of new drugs. The development of advanced devices that enable reliable and sensitive detection of these species is therefore important.

Central to detection is the signal transduction associated with selective recognition of a biological or chemical species of interest. Planar semiconductors can serve as the basis for chemical and biological sensors in which detection can be monitored electrically and/or optically. For example, a planar field effect transistor (FET) can be configured as a sensor by modifying the gate oxide (without gate electrode) with molecular receptors or a selective membrane for the analyte of interest. Binding of a charged species then results in depletion or accumulation of carriers within the transistor structure. An attractive feature of such chemically sensitive FETs is that binding can be monitored by a direct change in conductance or related electrical property, although the specificity for different biological molecules is limited.

The physical properties limiting sensor devices fabricated on planar semiconductors can be readily overcome by exploiting nanoscale FETs. In this regard, nanoscale sensors based on nanowires and nanotubes have received considerable recent attention. Nanowires and nanotubes have the potential for very high sensitivity (single-molecule detection in some cases) since the depletion or accumulation of charge carriers, which are caused by the binding of a charged molecule at the surface of the nanowire/nanotube, can affect the entire cross-sectional conductional pathway of these nanostructures. Furthermore, the small size of the nanowires and nanotubes combined with recent advances in assembly suggest that dense arrays of sensors could be prepared.

Research in this area has shown that nanowire FET devices can be functionalised with immobilised probe molecules such as surface receptors for the detection of specific molecular species in solution. The first published example demonstrating the ability of a nanowire FET to detect species in solution dates back to 2001, where a p-type Si nanowire device was used as a pH sensor by chemical modification of the silicon oxide surface [Y. Cui et al, Science, 293, 1289 (2001)]. This silicon nanotube-based device was subsequently modified to enable it to detect the presence of various proteins.

Using the same principle, such sensors have been used as tools for drug discovery, where the binding or inhibition of binding was solved as an increase or decrease in conductance, respectively [W. U. Wang et al, PNAS, 102, no. 9, 3208 (2005)]. In addition, single-stranded DNA fragments have been detected as an increase in conductance using a nanowire surface modified with peptide nucleic acid (PNA) receptors [J. Hahm et al, Nano Letters, 4, no. 1, 51 (2004)].

Further research has demonstrated the detection of a virus using an antibody receptor [F. Patolsky et al, PNAS, 101, no. 39, 14017 (2004)], wherein the binding and the release of the virus particles caused a change in the conductance of the nanowire device.

Whilst nanowire-based sensors offer a number of key benefits with respect to other technologies (direct, label-free, real-time detection, ultrahigh sensitivity, high selectivity, potential for integration into arrays on a massive scale), the above-mentioned devices also have their drawbacks. Reports of the use of FETs to directly sense the presence of biological molecules have shown inconsistent results, partly due to the complexity of the charged species being measured. In addition, such devices cannot be reused after the sensing event and must therefore be disposed of. Furthermore, the correct attachment of the receptor molecules to ensure highly specific binding requires sometimes complicated surface functionalisation.

Development of surface chemistry to couple biological molecules to a surface is a common problem in the development of sensors, and numerous solutions exist. One solution exploits the capacity of certain types of lipid molecules to form membranes, for example the plasma membrane that encloses the cytoplasm of many types of biological cells. Some types of receptor molecules have evolved to bind their analyte when they are embedded in lipid membranes. This specific receptor-analyte recognition leads to an alteration of some electrochemical property of the membrane, such as transmembrane conductance or capacitance.

Recent work has suggested that lipid membranes can serve as functional interfaces between the biological analyte and the nanoelectronic sensor [N. Misra et al, PNAS, 106, no. 33, 13780 (2009)]. In this study, Si nanowires were covered by a continuous lipid bilayer membrane to form a shield between the nanowire and the species in solution. The incorporation of transmembrane peptide pores enabled ionic species to transport across the membrane and generate an ionic-electronic signal. This work suggests that lipid membrane-coated nanowire devices incorporating functional membrane proteins could serve as versatile platforms for developing biosensors that are based on the functionality of the transmembrane protein pores.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

SUMMARY

According to a first aspect, there is provided an apparatus for the selective release of a bound species based on the presence of an analyte, the apparatus comprising:
  a first and second receptor species,
    the first receptor species linked with a bound species and configured to interact with an analyte to form a first intermediate complex, the bound species for causing increased porosity of a membrane of an in-contact analyte sensor apparatus to correspondingly increase exposure of a sensing element of the analyte sensor apparatus to allow for production of a detectable electrical signal which can be used to sense the presence of the analyte, the second receptor species for interacting with the first intermediate complex to form a second intermediate complex; and a cleaving species, the cleaving species configured to interact with the second intermediate complex to release the bound species for use in sensing the presence of the analyte.

The terms "interact" and "interacting" may imply direct or indirect interaction. Furthermore, the terms "interact" and "interacting" may imply binding of one species to another.

The first and second receptor species may be capable of interacting specifically with the analyte. The intermediate complex may be formed by specific interaction of the analyte with the first receptor species. The second intermediate complex may be formed by specific interaction of the analyte with the second receptor species. The first and second receptor species may be antibodies, but could be other affinity agents capable of specific interaction with the analyte. The antibodies may comprise immunoglobulin molecules, such as IgG molecules. The antibodies may be monoclonal antibodies or polyclonal antibodies. Two or more monoclonal antibodies may be configured to interact with the same antigen.

The analyte may be an antigen. The analyte may be a biological or chemical species of sufficient size and structure that the affinity reagent (herein described as an antibody) can recognise and bind with sufficient specificity and avidity. The analyte may be a pathogen. The analyte may be a viral, bacterial, fungal, eukaryotic or prionic pathogen.

The bound species may be an enzyme. The bound species may also be referred to as a "signal generating species". The bound species may be an enzyme capable of catalysing the hydrolysis of lipids. The bound species may be lipase. The bound species may be bound to the first receptor species by a chemical bond which is known to specifically break in the presence of the cleaving species.

The cleaving species may be configured to release the bound species by cutting the link between the first receptor species and the bound species. Cleavage may occur in such a way that neither the bound species nor the receptor species suffer damage that compromises their activity. The cleaving species may be configured to release the bound species from the first receptor species through cleavage of disulphide bonds, although other mechanisms may be used for cleavage. The cleaving species may be a reducing agent (reductant).

The first and second receptor species may be located at first and second respective regions of a first piece of absorbent material. The first piece of absorbent material may be configured to allow liquid to flow through the first piece of absorbent material by capillary action. The first piece of absorbent material may be configured to allow a first liquid to flow consecutively through the first and second regions.

The first liquid may comprise the analyte. The first liquid may comprise a solution of the analyte. The flow of first liquid through the first region may be configured to allow the analyte to interact with the first receptor species to form the first intermediate complex. The flow of first liquid through the second region may be configured to allow the first intermediate complex to interact with the second receptor species to form the second intermediate complex.

The apparatus may comprise a second piece of absorbent material. The second piece of absorbent material may be connected to the first piece of absorbent material at the second region to allow a flow of second liquid through the second region. The second liquid may comprise the cleaving species. The second liquid may flow in a different direction to the first liquid. The flow of second liquid may be a cross flow through the second region. The flow of second liquid may be configured to allow the cleaving species to interact with the second intermediate complex to release the bound species. The second liquid may be configured to transfer the bound species from the first piece of absorbent material to the second piece of absorbent material after the bound species has been released.

The first and second pieces of absorbent material may form part of a lateral flow assay. The first and second pieces of absorbent material may be configured such that their respective long axes are perpendicular to one another and lie in (or substantially in) the same plane. The first and second pieces of absorbent material may be configured such that their respective long axes are perpendicular to one another and lie in different planes. The first and second pieces of absorbent material may be configured such that their respective long axes lie at an angle other than 90 degrees with respect to one another in (or substantially in) the same plane. The first and second pieces of absorbent material may be configured such that their respective long axes lie at an angle other than 90 degrees with respect to one another in different planes.

The first and second pieces of absorbent material may have respective first and second ends. The first and second pieces of absorbent material may be configured to allow liquid to flow from their respective first ends to their respective second ends. The first and second pieces of absorbent material may each comprise a sample pad at their respective first ends. The first and second liquids may be applied to the sample pads of the first and second pieces of absorbent material respectively to allow the first and second liquids to flow from the first end to the second end of the respective pieces of absorbent material. The first piece of absorbent material may comprise a wicking pad at its second end. The wicking pad may be configured to collect any species which have reached the end of the first piece of absorbent material. The wicking pad may be configured to draw the first liquid along the first piece of absorbent material.

The apparatus may comprise an analyte sensor apparatus. The analyte sensor apparatus may comprise a sensing element, the external surface of which may comprise a membrane configured to inhibit exposure of the sensing element. The analyte sensor apparatus may be connected to the second piece of absorbent material. The connection between the analyte sensor apparatus and the second piece of absorbent material may allow the bound species to interact with the analyte sensor apparatus to cause increased porosity of the membrane.

The dimensions of the sensing element may be on the macroscale (e.g. cm or mm), microscale (e.g. μm) or nanoscale (e.g. nm). The sensing element may be formed from an intrinsic or doped semiconducting material. The semiconducting material may be a p-type or n-type semiconducting material. The sensing element may be a silicon sensing element.

The sensing element may comprise a planar substrate. The sensing element may comprise one or more nanowires. The term "nanowire" has been used to encompass nanotubes and such like. The nanowire may be a hollow/solid tube.

The apparatus may comprise a fluid medium. The fluid medium may comprise a charged species configured to provide an ionic gradient across the membrane. On the other hand, the fluid medium may comprise a charged species configured to produce a detectable electrical signal when in contact with the sensing element.

The membrane may be configured to be impervious to the charged species comprised in the fluid medium. The increased porosity of the membrane caused by release of the bound species may allow the charged species to diffuse through the created pores in the membrane from the fluid medium. Diffusion of the charged species through the created pores may cause a change in charge concentration at the exposed surface of the sensing element.

The charged species may comprise positively or negatively charged ions. The charged species may be a charged atomic species (such as a hydrogen ion) or a charged molecular species. The charged species may be a charged subatomic particle such as a proton or electron. Diffusion of the ions through the membrane from the fluid medium may cause a change in pH at the external surface of the sensing element.

The sensing element may be coated by a membrane. The membrane itself may comprise any material which, until pores have been created in the membrane, is capable of inhibiting exposure of the sensing element to the fluid medium. The membrane may comprise a lipid or other molecules that form a barrier to certain species whose proximity to the sensing element may or may not change its conductance. In particular, the membrane may comprise a lipid, a phospholipid or mixtures of the two. The lipid may be dioleoyl phosphatidylcholine (DOPC). The DOPC may be doped with a fluorescent lipid probe such as NBD-PE (1,2-dioleoyl-sn-glycero-3-phosphoethanolamine-N-(7-nitro-2-1,3-benzoxadiazol-4-yl)).

The analyte sensor apparatus may form part of a field-effect transistor. The analyte sensor apparatus may form part of a nanowire field-effect transistor. The analyte sensor apparatus may comprise a plurality of nanowires on a substrate. The analyte sensor apparatus may comprise one or more arrays of nanowires on a substrate. Advantageously, the respective arrays may be configured to be spaced apart from one another on the substrate such that the sensor is able to perform multiplexed sensing experiments. The analyte sensor apparatus may be integrated within a microfluidic system.

The analyte sensor apparatus may further comprise source and drain electrodes. The source and drain electrodes may be electrically connected to the sensing element such that an electrical current may flow from the source electrode through the sensing element to the drain electrode when a potential difference is applied across the source and drain electrodes. The apparatus may be configured such that electrical connectors are electrically connected to the source and drain electrodes to apply the potential difference. The apparatus may be configured such that the electrical connectors are removably connected to the source and drain electrodes. The apparatus may be configured such that the source and drain electrodes are electrically insulated from the fluid medium. The apparatus may be configured such that the conductance of the sensing element varies with charge concentration at the external surface of the sensing element.

The apparatus described herein may comprise a chamber for housing the analyte sensor apparatus. A portable electronic device may comprise one or more features of the apparatus described herein. For example, the portable electronic device may comprise one or more of the chamber and analyte sensor apparatus. The other apparatus features may be attachable to (or capable of being added to) the portable electronic device. For example, the first and second strips may be attachable to the chamber of the portable electronic device. The various species may then be added to the first and second strips via a microfluidic system. The portable electronic device may also comprise the microfluidic system.

The portable electronic device may be a hand-portable electronic device which may be hand-held in use (although it may be placed in a cradle in use). Such hand-portable electronic devices include so-called Personal Digital Assistants (PDAs).

The portable electronic device according to one or more disclosed aspects/embodiments may provide one or more audio/text/video communication functions (e.g. tele-communication, video-communication, and/or text transmission (Short Message Service (SMS)/Multimedia Message Service (MMS)/emailing) functions), interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

According to a further aspect, there is provided a method of selectively releasing a bound species based on the presence of an analyte, the method comprising:

using/providing an apparatus, the apparatus comprising a first and second receptor species and a cleaving species,
- the first receptor species linked with a bound species and configured to interact with an analyte to form a first intermediate complex, the bound species for causing increased porosity of a membrane of an in-contact analyte sensor apparatus to correspondingly increase exposure of a sensing element of the analyte sensor apparatus to allow for production of a detectable electrical signal which can be used to sense the presence of the analyte,
- the second receptor species for interacting with the first intermediate complex to form a second intermediate complex,
- the cleaving species configured to interact with the second intermediate complex to release the bound species for use in sensing the presence of the analyte; and exposing the apparatus to the analyte to allow for production of a detectable electrical signal which can be used to sense the presence of the analyte.

According to a further aspect, there is provided a computer program for detecting the presence of an analyte using an apparatus, the apparatus comprising:

a first and second receptor species,
- the first receptor species linked with a bound species and configured to interact with an analyte to form a first intermediate complex, the bound species for causing increased porosity of a membrane of an in-contact analyte sensor apparatus to correspondingly increase exposure of a sensing element of the analyte sensor apparatus to allow for production of a detectable electrical signal which can be used to sense the presence of the analyte,
- the second receptor species for interacting with the first intermediate complex to form a second intermediate complex; and a cleaving species, the cleaving species configured to interact with the second intermediate complex to release the bound species for use in sensing the presence of the analyte, the computer program comprising code to detect an electrical signal produced from the apparatus to detect the presence of the analyte.

According to a further aspect, there is provided the use of an apparatus for selectively releasing a bound species based on the presence of an analyte, the use comprising:

providing an apparatus, the apparatus comprising a first and second receptor species and a cleaving species,
- the first receptor species linked with a bound species and configured to interact with an analyte to form a first intermediate complex, the bound species for causing increased porosity of a membrane of an in-contact analyte sensor apparatus to correspondingly increase exposure of a sensing element of the analyte sensor apparatus to allow for production of a detectable electrical signal which can be used to sense the presence of the analyte, the second receptor species for interacting with the first intermediate complex to form a second intermediate complex, the cleaving species configured to interact with the second intermediate complex to release the bound species for use in sensing the presence of the analyte; and instructing exposure of the apparatus to the analyte to allow for production of a detectable electrical signal which can be used to sense the presence of the analyte.

The present disclosure includes one or more corresponding aspects, embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

DESCRIPTION OF SPECIFIC ASPECTS/EMBODIMENTS

Figure 1:
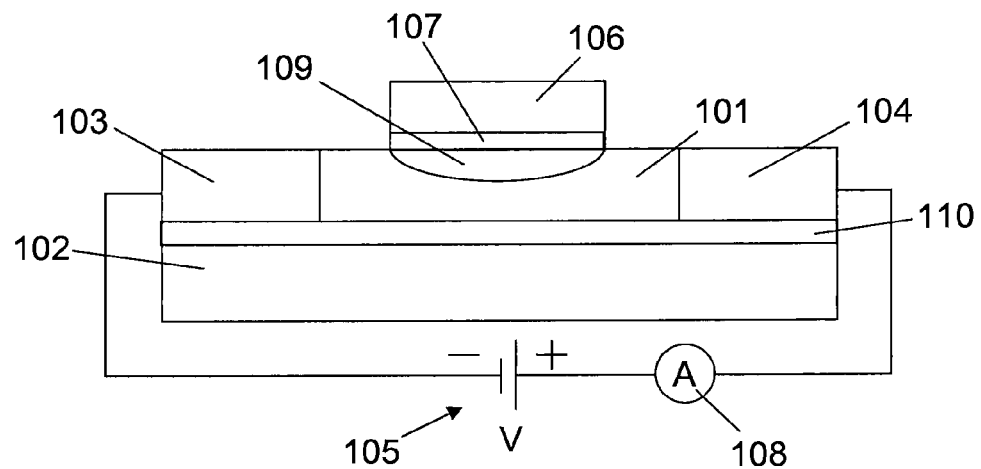
FIG. 1 illustrates schematically a planar field effect transistor.

As discussed in the background section, nanowires can be used to create highly sensitive and real-time electrically-based sensors for the detection of biological and chemical species. The underlying mechanism for nanowire sensors is a field effect that is transduced using field-effect transistors (FETs). In a standard (planar) FET, as illustrated in FIG. 1, a semiconductor such as p-type silicon 101 is supported on a substrate 102 (coated with an electrically insulating layer 110) and connected to metal source 103 and drain 104 electrodes. A current is injected and collected via the source and drain electrodes 103, 104, respectively, by applying a potential difference 105 across the semiconductor. The conductance of the semiconductor between the source and drain electrodes is switched on and off by a third electrode, the gate electrode 106, capacitively coupled through a thin dielectric layer 107. Conductance may be determined by measuring the current through the semiconductor (using an ammeter 108, for example) and dividing by the potential difference. With p-type silicon (or another p-type semiconductor), application of a positive gate voltage depletes charge carriers (creating a depletion region 109 in the semiconductor) and reduces the conductance, whilst applying a negative gate voltage leads to an accumulation of charge carriers (creating a conductive channel) and an increase in conductance. The dependence of conductance on gate voltage makes FETs natural candidates for electrically-based sensing since the electric field resulting from the binding of a charged species to the gate dielectric is analogous to applying a voltage using a gate electrode.

Figure 2:
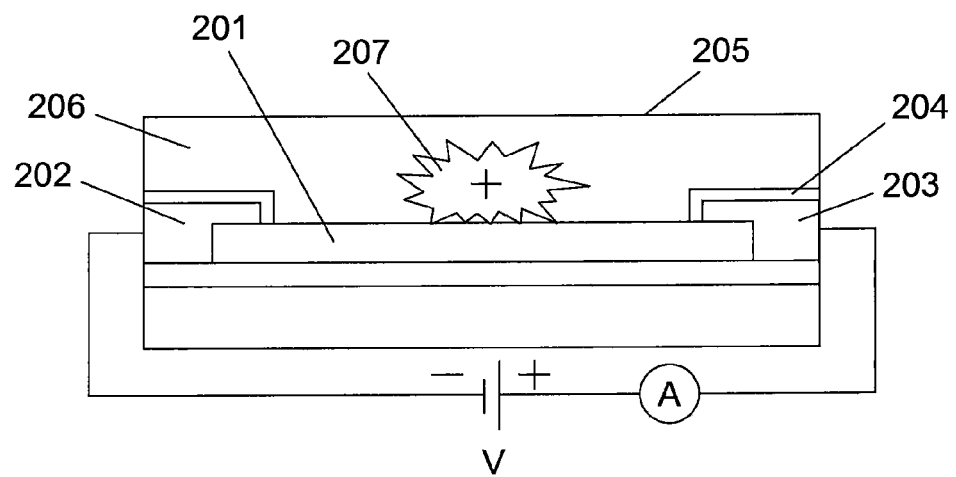
FIG. 2 illustrates schematically a nanowire field effect transistor.

In a nanowire FET (FIG. 2), the planar semiconductor is replaced by one or more nanowires 201 and the gate electrode is removed. Specific sensing can achieved by linking a recognition group to the surface of the nanowire. Silicon nanowires with their natural oxide coating allow multiple approaches to this receptor linkage, since extensive data exists for the chemical modification of silicon oxide or glass surfaces in planar chemical and biological sensors. The sensor device illustrated further incorporates source 202 and drain 203 electrodes which are insulated from the environment by a dielectric coating 204 so that only those processes occurring at the nanowire surface contribute to the electrical signal.

The sensor device may also incorporate a microfluidic system. Microfluidics is the science of designing, manufacturing and formulating devices and processes that deal with the behaviour, precise control and manipulation of fluids that have volumes on a sub-millilitre scale (microlitres, nanolitres or possibly even picolitres). The devices themselves have dimensions ranging from millimetres down to micrometers. The behaviour of fluids at this scale can differ from macrofluidic behaviour in that factors such as surface tension, energy dissipation and fluid resistance start to dominate the system. Microfluidic systems include a number of components (such as pumps, valves, seals and channels etc) specifically adapted to control such small volumes of fluid. Microfluidic systems have diverse and widespread potential applications. In particular, microfluidic biochips utilise microfluidic systems to integrate assay operations (such as detection, sample pretreatment and sample preparation) on a single chip. A microfluidic channel 205 for delivery of the solutions 206 being examined can be seen in FIG. 2.

When the sensor device with surface receptor is exposed to a solution containing an analyte molecule 207 that, for example, has a net positive charge in aqueous solution, specific binding causes an increase in the surface positive charge and a decrease in conductance for a p-type nanowire device. It is of course possible to form a sensing device using an n-type nanowire instead of a p-type nanowire.

Figure 3:
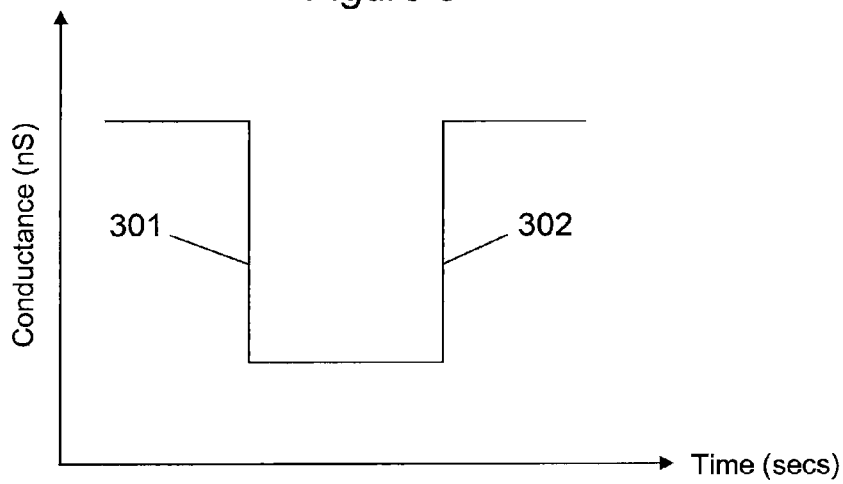
FIG. 3 illustrates schematically a typical conductance versus time plot for a nanowire sensor.
Figure 4:
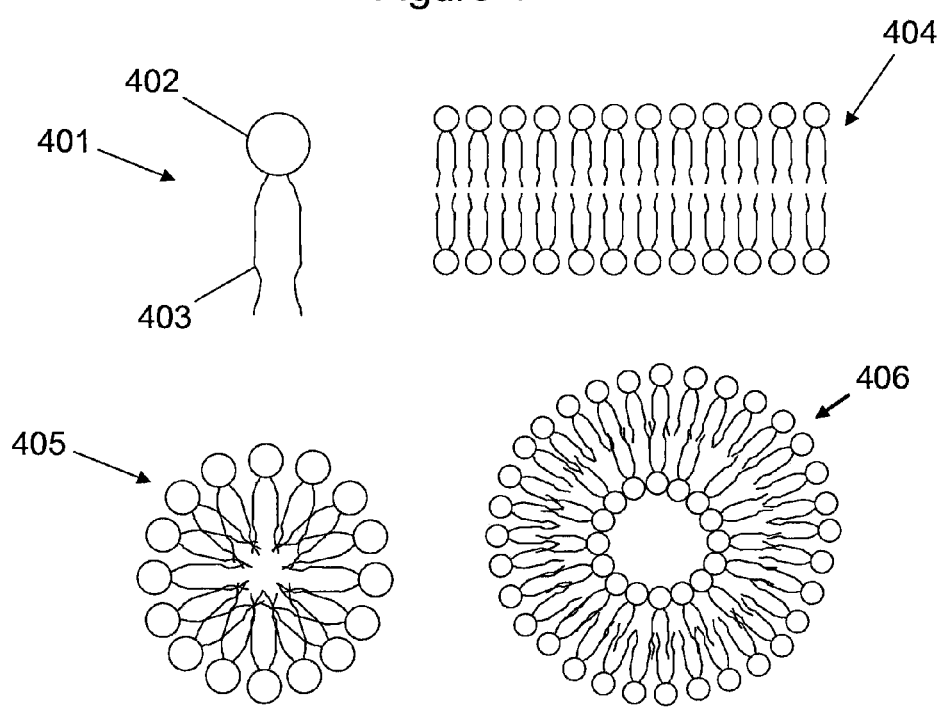
FIG. 4 illustrates schematically a (phospho)lipid molecule, a lipid bilayer, a lipid micelle and a liposome.

An example of a typical conductance versus time plot for a p-type nanowire sensor is given in FIG. 3, which shows a decrease in conductance 301 when an analyte molecule that has a net positive charge binds to the surface of the nanowire. Subsequent detachment of the analyte species then results in an increase in conductance 302 to the original value.

As mentioned earlier, reports of existing nanowire FETs have shown inconsistent behaviours, cannot be reused after the sensing event, and show high analyte specificity only when a recognition element is used in the sensing mechanism. There will now be described an apparatus and associated methods that may or may not overcome one or more of these issues.

The examples of the apparatus and methods described herein incorporate a lipid bilayer on the surface of the nanowire sensing element. A lipid bilayer is a thin membrane made up of two layers of lipid molecules 401. Lipids are small amphiphilic molecules, meaning they contain both hydrophilic 402 and hydrophobic 403 groups. The amphiphilic nature of some lipids allows them to form structures such as bilayers 404, micelles 405 and liposomes (or vesicles) 406 in an aqueous environment depending on the concentration of the solution. Natural lipid bilayers are usually made mostly of phospholipids, which have a hydrophilic head and two hydrophobic tails. Phospholipids are similar to lipids except that they may have one or more phosphate groups covalently bonded to the hydrophilic head. Lipids self-assemble into these structures because of the hydrophobic effect, which creates an energetically unfavourable interaction between the hydrophobic tails and the surrounding water. Therefore, a lipid bilayer is held together by non-covalent forces that do not involve the formation of chemical bonds between individual molecules.

In nature, lipid bilayers form a continuous barrier around biological cells. The cell membrane of almost all living organisms and many viruses are made of a lipid bilayer, as are the membranes surrounding the cell nucleus and other subcellular structures. The cell membrane is the barrier that keeps ions, proteins and other molecules where they are needed and prevents them from diffusing into areas where they should not be. Lipid bilayers are ideally suited to this role because, even though they are only a few nanometers thick, they are impermeable to most water-soluble molecules. Bilayers are particularly impermeable to ions, which allow cells to regulate salt concentrations and pH.

Figure 5:
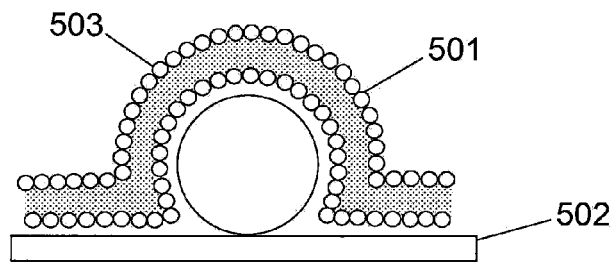
FIG. 5 illustrates schematically a cross-section of a nanowire coated with a lipid bilayer.

FIG. 5 shows a cross-sectional view of a nanowire sensing element 501 supported on a substrate 502 and coated with a lipid bilayer membrane 503. The lipid bilayer may be formed on the nanowire surface by spontaneous fusion of liposomes. This is achieved by exposing the nanowire surface to liposomes of phospholipid molecules. A hydrophilic surface such as the silicon oxide coating on a silicon nanowire or similar sensing element facilitates spontaneous fusion of the liposomes on the surface to create a conformal lipid bilayer.

The sensing mechanism of the present disclosure, which will now be described in detail, involves degradation of the lipid bilayer membrane using a pore-inducing species. The apparatus and method of the present disclosure incorporates the use of a modified lateral flow immunoassay system.

With reference to FIG. 6, a lateral flow system (also known as a lateral flow test or a lateral flow assay) is a simple device used to detect the presence of a target analyte. Most commonly, these devices are used for medical diagnostics either for home testing (e.g. pregnancy tests), point of care testing, or laboratory use. Lateral flow systems are a form of immunoassay in which the test sample flows along a solid substrate (or strip) via capillary action.

Figure 6A:
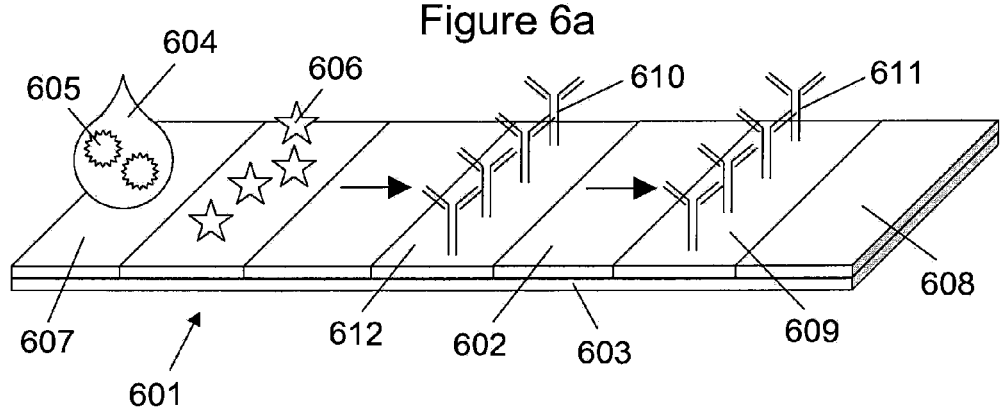
FIG. 6a-d illustrates schematically a standard lateral flow system.
Figure 6B:
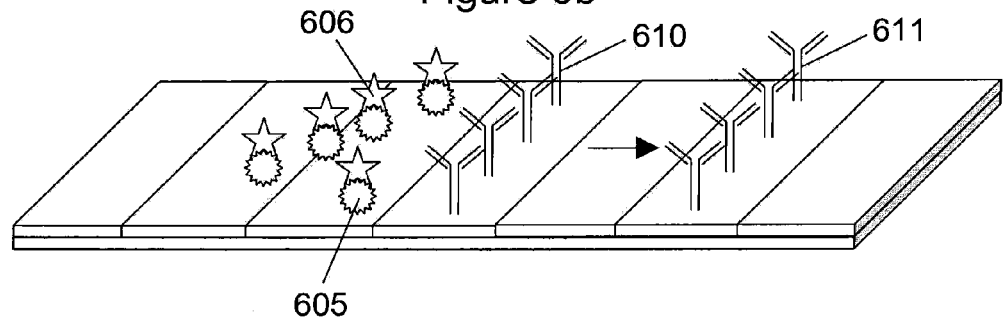
Figure 6C:
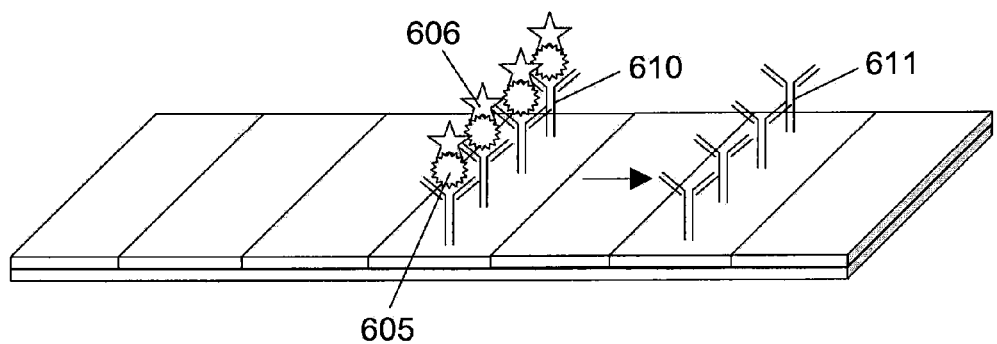
Figure 6D:
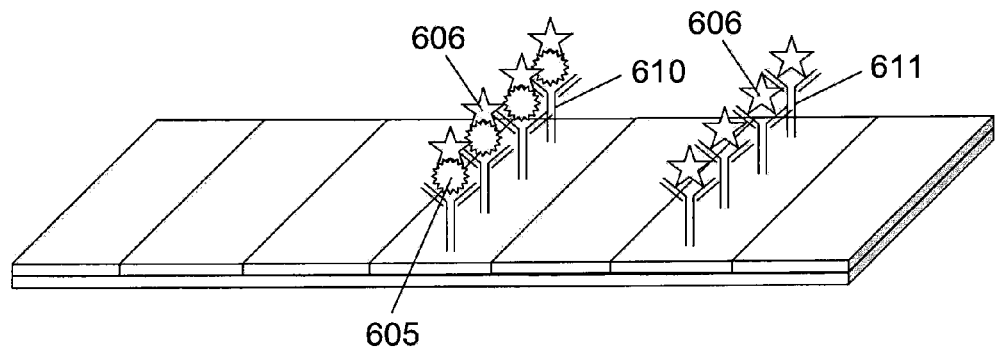

The strip 601 (FIG. 6a) consists of an absorbent material 602 on a stiff backing 603. When a sample 604 (a liquid containing the analyte 605 of interest) is applied to one end of the strip, it encounters and binds to a signal generating system 606 (FIG. 6b). The signal generating system 606 is typically a coloured particle such as gold (red) or latex (blue) functionalised with an affinity receptor (typically an antibody) that binds to the target analyte. The sample then flows from one end of the strip (the sample pad 607) to the other end of the strip (the wicking pad 608). As the sample diffuses along the length of the strip (see FIG. 6b for example), it passes two regions impregnated with high concentrations of specific antibodies, the test line 612 and the control line 609. The test line antibodies 610 are capable of binding to the analyte 605 but not the signal generating system 606 unless it is bound to the analyte 605, whilst the control line antibodies 611 are capable of binding to the signal generating system 606 regardless of analyte presence. When the sample reaches the test line (FIG. 6c), binding of the analyte 605 to the test line antibodies 610 causes a change in colour at the test line due to the presence of the signal generating system 606 which is bound to the analyte 605.

If the analyte is not present in the sample, no binding occurs at the test line antibodies 610 and there is no change in colour. The control line 609 is then used to confirm that the test ran successfully, that is, that the sample 604 travelled the length of the test strip 601. Confirmation is achieved when any signal generating system 606 (bound or unbound to the analyte 605) binds to the control line antibodies 611 (FIG. 6d) causing a change in colour. Appearance of two lines therefore indicates a positive result, whilst a negative test produces only the control line. If only the test line appears, or if no lines appear, the test is invalid and must be repeated.

The apparatus and method of the present disclosure incorporates a species (referred to herein as the "bound species") into the lateral flow system that can be specifically released from the test line on the addition of a release system (referred to herein as the "cleaving species"). On release, this species may or may not be transported to another location in the device where it drives the generation of a signal that is measured electronically. In this document the cleaving species is described as an enzyme that can generate pores in a membrane, leading to a change in conductivity of a nanowire sensing element. This concept could be applied to multiple different mechanisms for generating a signal, for instance the release of an optically active entity where the signal is the optical measurement of its presence in a new location.

In this disclosure the "bound species" is an enzyme (a lipase) selected on its ability to create pores in the lipid bilayer of an in-contact analyte sensor apparatus. Lipase is a term defining a water-soluble enzyme that catalyses the hydrolysis of ester bonds in lipids (and these enzymes are one of the most commonly manufactured category of industrial enzyme). Lipase is therefore a suitable candidate for this role. The specific configuration of the apparatus allows the bound species access to the membrane only when the sample contains the analyte of choice. In effect, this may serve as a specific and indirect sensing technique for detecting the presence of an analyte in solution. Implementation of this technique is illustrated in FIG. 7.

Figure 7A:
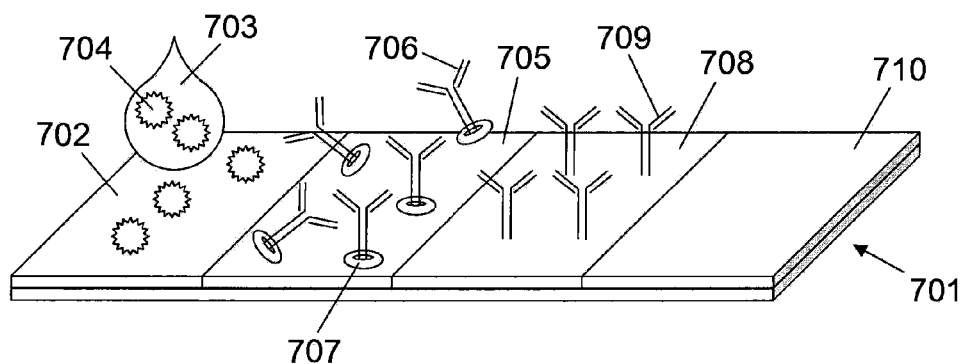
FIG. 7a-g illustrates schematically a modified lateral flow system incorporating a lipid-coated nanowire.
Figure 7B:
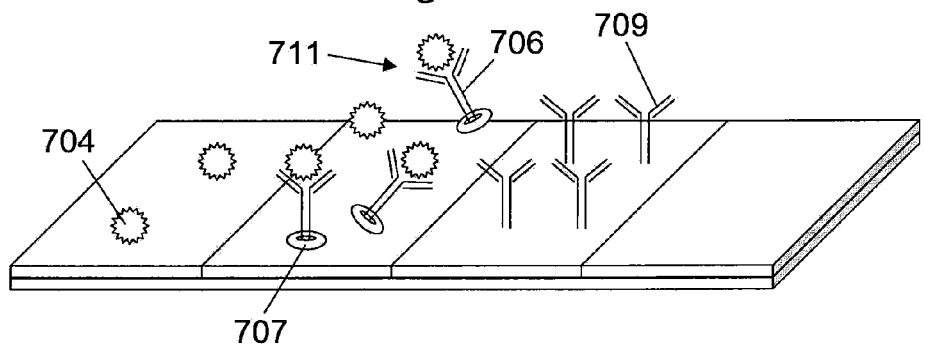
Figure 7C:
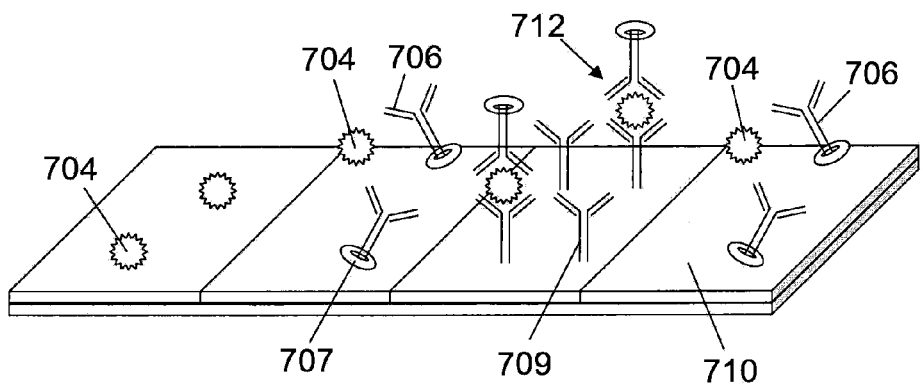

The apparatus comprises a first piece (strip) of absorbent material 701 comprising a sample pad 702, first 705 and second 708 regions, and a wicking pad 710. A liquid sample 703 containing the target analyte 704 is deposited onto the sample pad (FIG. 7a). The first region 705 is treated with a first receptor species 706 linked with a bound species 707. The second region contains a second receptor species 709 which may or may not be identical to the first receptor species 706. As with the standard lateral flow system (FIG. 6), capillary forces draw the liquid along the length of the strip. The liquid flows into the wicking pad 710 once it reaches the end of the strip.

When the liquid arrives at the first region 705 (FIG. 7b), e.g. by direct application to that region or a region upstream of the first region 705, a proportion of the available analyte 704 is bound by the first receptor species 706 to form a first intermediate complex 711. Saturation binding of the first receptor species may occur but is not essential for signal generation. As time progresses, the liquid (which now also comprises the first intermediate complex 711) migrates along the strip and reaches the second region of the strip (FIG. 7c) where the first intermediate complex 711 binds to the second receptor species 709 through the analyte 704 to form a second intermediate species 712. Any unbound analyte 704 and first receptor species 706 continue flowing towards the wicking pad 710 and do not bind to the second receptor species 709.

The apparatus may further comprise a control line (similar to the control line 609 of FIG. 6) to confirm whether or not the sample 703 has travelled the length of the first strip 701. The control line (not shown) may comprise a control line species (similar to the control line antibodies 611 shown in FIG. 6, or some other receptor species) capable of binding to the analyte 704, whereby binding of the control line species to the analyte 704 produces a change in colour. The control line species may be located at the wicking pad 710.

Furthermore, the apparatus may comprise a signal generating system (similar to the signal generating system 606 of FIG. 6) capable of binding to the analyte 704. With this approach, the signal generating system (not shown) could be used to produce a change in colour at the control line when it binds to the control line species.

In both examples, no change in colour at the control line after the first liquid 703 has been applied to the first strip 701 would indicate that the test is invalid and should be repeated.

Figure 7D:
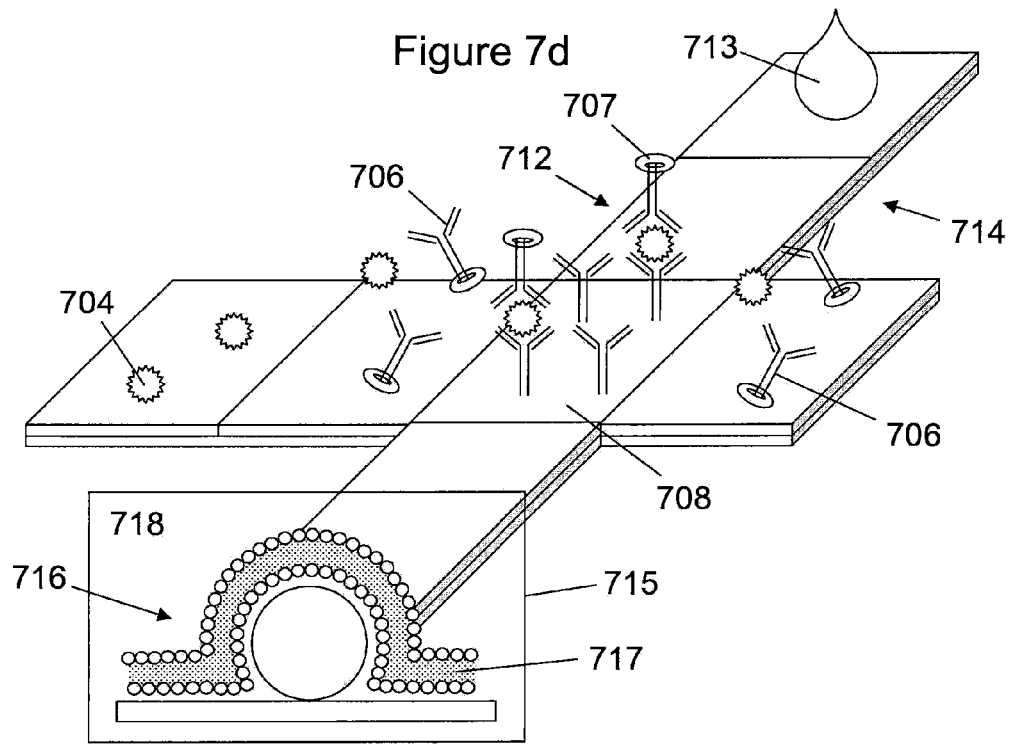
Figure 7E:
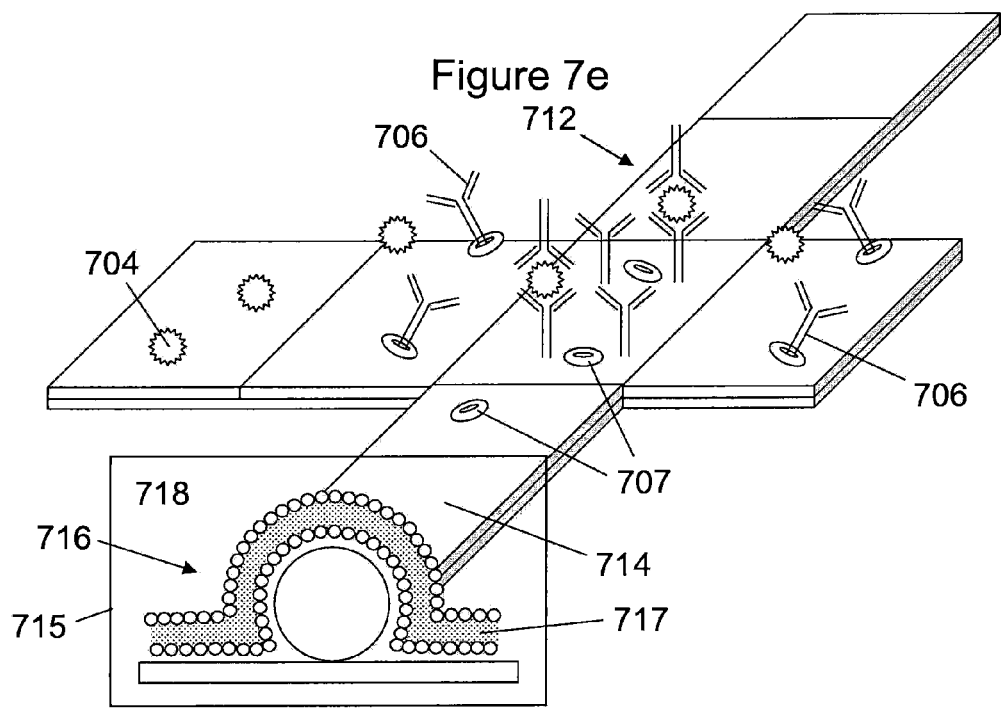
Figure 7F:
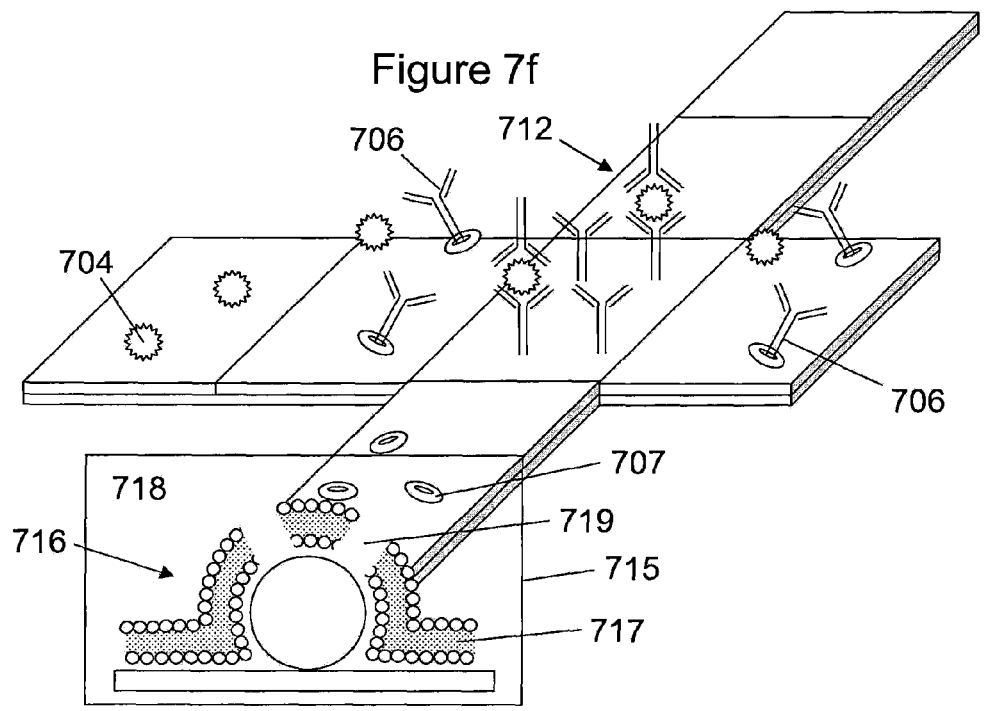

Whilst the liquid is progressing (or has progressed) along the length of the first strip 701, a second liquid 713 comprising a cleaving species (a chemical that will specifically cleave the linker between the affinity agent and the bound species) is added to the second region 708 of the first strip. As shown in FIG. 7d, the second liquid 713 is introduced via a second piece (strip) of absorbent material 714 which is connected to the second region 708, though other addition mechanisms could be used. The second strip is configured to allow the second liquid 713 to flow through the second region (cross flow) such that the cleaving species is able to interact with the second intermediate complex 712, though other methods for this addition can be used. The cleaving species 713 selectively cuts the link between the first receptor species 706 and the bound species 707 thereby releasing the bound species 707 (FIG. 7e). As shown in FIGS. 7d-g, the second strip is connected to a chamber 715 containing a membrane-coated nanowire 716. The cross-flow of second liquid 713 carries the released bound species 707 from the second region 708 of the first strip along the second strip 714 to the chamber 715 for interaction with the lipid membrane 717.

The chamber further contains an ionic solution 718. When the membrane-coated nanowire 716 is immersed in an ionic solution (for instance, an aqueous buffer solution), the lipid bilayer 717 prevents any charged species from contacting the nanowire (sensor) surface. Therefore, the lipid bilayer can be used to maintain an ionic gradient across the membrane. Since phospholipid membranes are impermeable to hydrogen ions (or protons, $H^+$), they are able to maintain an aqueous pH gradient across the membrane, at least for a certain period of time.

Figure 7G:
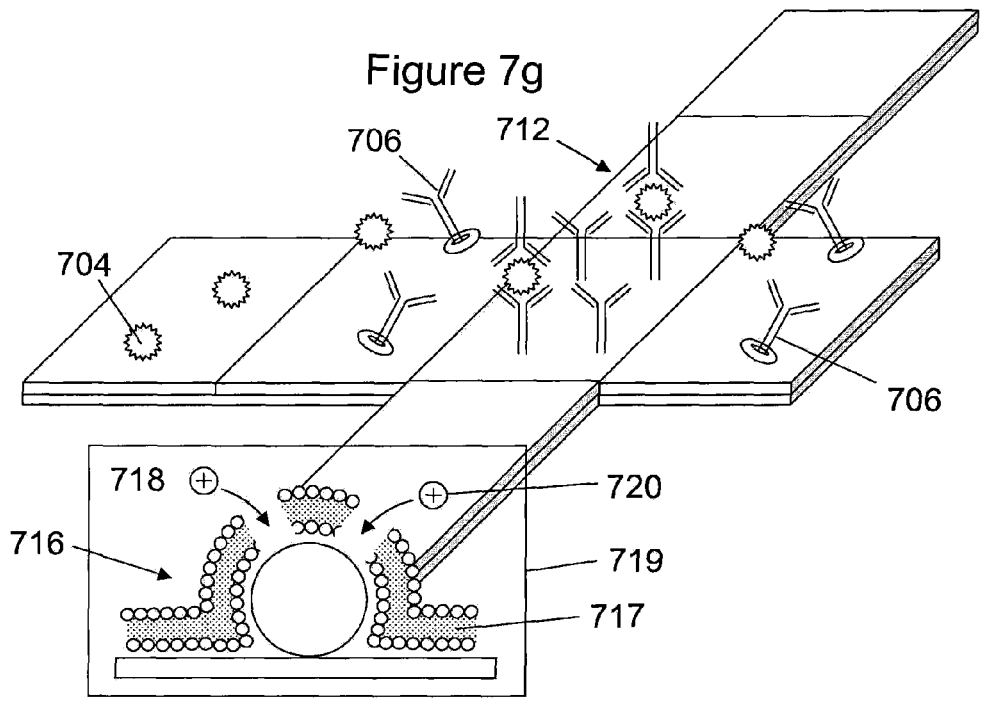

Once the bound species 707 enters the nanowire chamber 715 (FIG. 7f), it catalyses the hydrolysis of the lipid molecules to minor components, inducing pores 719 in the membrane 717. The creation of pores in the membrane allows ions 720 in the solution 718 to cross through the membrane 717 and interact with the nanowire surface (FIG. 7g). The diffusion of ions 720 through the membrane 717 is driven by the ionic gradient. Changes in conductivity caused by the presence of charged species 720 at the surface of the nanowire can then be detected. The aqueous buffer solution 706 may be any buffer solution which allows unambiguous detection of the charged species by the exposed nanowire sensing element. The aqueous buffer solution 706 may comprise (but is not be limited to) one or more of the following: sodium ions, magnesium ions and protons.

Figure 10:
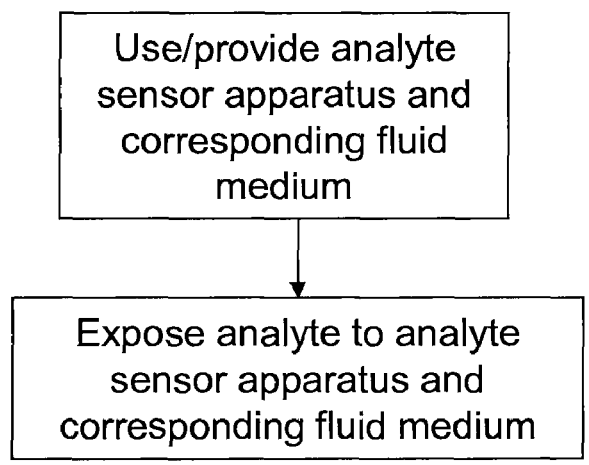
FIG. 10 illustrates schematically a method of sensing an analyte.

An important feature of this apparatus and method (the key steps of which are illustrated schematically in FIG. 10) is that the bound species 707 can only access the chamber 715 (and therefore the membrane-coated nanowire 716) if the first intermediate species 711 is bound to the second receptor species 709. Given that the liquid sample 703 must contain the specific analyte of interest 704 in order to form the first intermediate species 711 and subsequently bind to the second receptor species 709, the detected change in conductance is indicative of the presence of that particular analyte 704. Furthermore, since the time period between the bound species reaching the coated nanowires and the measured increase in porosity of the membrane are proportional to the amount of bound species 707 released (and therefore the amount of analyte 704 present in the sample 703), the conductance of the nanowire can also be used to provide quantitative information on the analyte concentration. This method therefore provides a highly selective sensing mechanism without the need to bind the analyte 704 to the surface of the nanowire. The fact that the analyte 704 need not even be introduced to the chamber 715 containing the nanowire further illustrates the indirect nature of the sensing mechanism.

Figure 8:
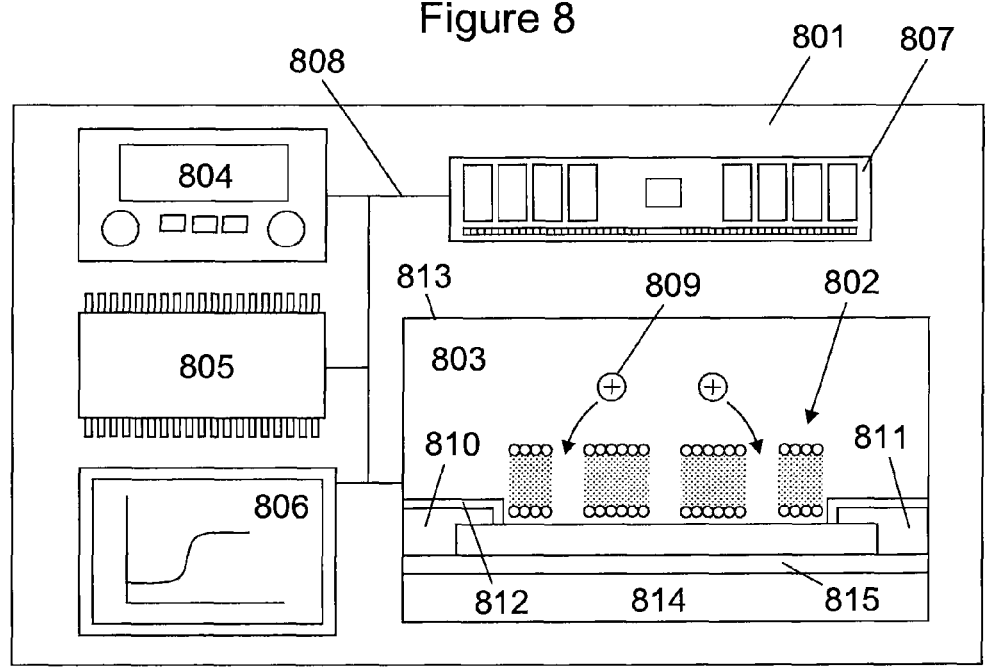
FIG. 8 illustrates schematically a device comprising the apparatus described herein.

FIG. 8 illustrates schematically a sensor device 801 comprising the apparatus of FIG. 7. For simplicity in the figure, the absorbent strips 701, 714 are not shown and the membrane-coated nanowire 716 is illustrated as a planar surface 802. The device also comprises a measurement apparatus 804, a processor 805, a display apparatus 806 and a storage medium 807, which may be (removably) electrically connected to one another by a data bus 808.

The sensor device further includes source 810 and drain 811 electrodes which are insulated from the environment by a dielectric coating 812, and a chamber 813 for containing the nanowire and ionic (buffer) solution 803. As mentioned earlier, the ionic solution 803 maintains an ionic gradient across the membrane. The sensor device may further comprise a microfluidic system for control of species into and out of the absorbent strips, as well as for delivery of the ionic solution 803 to the nanowire chamber 813. In particular, the microfluidic system may comprise a microfluidic channel for transferring the bound species from the second strip to the nanowire chamber. The second strip may be removably coupled to the chamber by the microfluidic channel.

The nanowire is supported on a substrate 814 which is coated with an electrically insulating layer 815 to isolate the electrical contacts 810, 811 from the supporting substrate 814. The nanowire may be formed using the vapour-liquid-solid (VLS) mechanism or catalytic chemical vapour deposition (CVD) procedures, and deposited on the surface of the supporting substrate 814 using a flow-alignment procedure. The electrical contacts 810, 811 may then be fabricated using a lithographic process.

The measurement apparatus 804 may be removably connected to the source and drain electrodes by electrical connectors (although in other embodiments it may be non-removably connected, e.g. hard-wired). The removable connections allow the nanowire to be disconnected and physically removed from the other device components for modification or replacement. Likewise, the absorbent strips may be removably connected to the chamber. The removable connections allow the absorbent strips to be detached and physically removed from the chamber for modification or replacement.

The measurement apparatus 804 is used to apply a potential difference across the nanowire, measure the current through the nanowire, and determine the conductance or other electrical property of the nanowire. The processor 805 receives the electrical data and processes the data for display on the display apparatus 806. This allows the electrical response of the nanowire to be observed visually. The processor 805 may also process the electrical data to determine the presence and, in certain cases, the quantity of the analyte species. The processor 805 may determine the presence and quantity of the analyte species by comparing the received data with data previously stored in a database to determine a match. On the other hand, the processor 805 may simply pass the processed data to the display apparatus 806 for manual analysis. The storage medium 807 is used to store the electrical data, and may also be used to store the database. The storage medium 807 may be a temporary storage medium such as a volatile random access memory, or may be a permanent storage medium such as a hard disk drive, flash memory or non-volatile random access memory.

If the measurement device is removably coupled to the source and drain electrodes, it is possible to supply a kit comprising the nanowire sensing apparatus (i.e. membrane-coated nanowire with electrical contacts and chamber) and lateral flow system (i.e. absorbent strips comprising one or more of the first receptor species, second receptor species, bound species and cleaving species). If the second strip is removably coupled to the chamber, the lateral flow system could be supplied separately from the nanowire sensing apparatus. The absorbent strips of the lateral flow system could even be supplied separately from one or more of the first receptor species, second receptor species, bound species and cleaving species. It may be useful to supply a control amount of the analyte so that one can confirm that the sensor is capable of detecting the analyte. Other experimental controls can be conceived to ensure that the sensor device meets the required performance characteristics. In this case, the analyte may be supplied on its own or with one or more of the other device components. The membrane-coated nanowire (with electrical contacts) and the lateral flow system may both be removably connected to the chamber. This would allow the chamber (possibly with ionic solution) to be supplied separately from the membrane-coated nanowire and lateral flow system.

The sensor device 801 may comprise either individual sensing elements 802 (e.g. nanowires) or arrays of sensing elements connected together in an electrical circuit. Each sensing element may be individually addressable both electronically, and in terms of liquid sample exchange via the microfluidic system. There are two formats of sensing element: one where multiple nanowires are covered with a single membrane, and another where a single nanowire is covered with a single membrane. In the former case, the nanowires may be individually addressed in the electronic circuit with the circuits operated in parallel, or multiple nanowires may be deposited between source 810 and drain 811 electrodes so that current is able to flow from one nanowire to the next.

In these examples, one or more nanowires are connected to a pair of metallic source 810 and drain 811 electrodes. The nanowires may be made from a uniform material for quality and performance. Typically the nanowires are crystalline with a thin layer of native oxide on the surface. The nanowire FETs can be fabricated by depositing the nanowires on either a hydrophilic or hydrophobic surface, and connecting the deposited nanowires to the source 810 and drain 811 electrodes using conventional photolithography. Passivation of the electrodes (obtained by coating them with an electrical insulator 812) is a critical step for these devices as they will operate in aqueous solution. The membrane coating may be continuous (i.e. covering the nanowires and supporting substrate 814) if the substrate is hydrophilic, or discontinuous (i.e. coating the nanowires but not the supporting substrate 814) if the substrate is hydrophobic. A reference gate electrode may be added to the sensing element (as per a standard planar FET).

The electronic circuit of sensing elements may be incorporated with the microfluidic system so that liquid can only follow prescribed routes to and from the sensing elements. The microfluidic system may comprise sample inlets, solution reservoirs, microchannels, waste reservoirs and, if required, pumping mechanisms. The exact architecture will vary depending on the particular species involved, and whether single sensing elements or arrays of sensing elements are employed. Each sensing element could have the option of being individually addressable and hence being operated in isolation from any other sensing elements in terms of both the microfluidics and the electronic control mechanisms.

The sensing element may be connected to a microchannel comprising an inlet and an outlet for delivering solutions. To simplify waste removal, the solution in the microchannel may be configured to flow in one direction from the inlet to the outlet. The solution reservoirs will typically contain (but are not be limited to) a supply of lipids to generate the membrane, and reaction buffers at different pHs for the correct functioning of the sensing mechanism.

The sensing mechanism requires a highly specific binding event between the target analyte 704 and the first 706 and second 709 receptor species. Receptors fulfilling these requirements include mammalian antibodies. There has been extensive research into the nature and identity of the analytes that can be recognized by mammalian antibodies. In general the targets must be above a certain size in order to form a sufficient number of chemical interactions with the analyte binding site of the antibody so that specificity and avidity are achieved. Hence antibodies are highly unlikely to recognize monoatomic ions such as hydrogen ions or metal ions. However, antibodies will recognize and bind larger molecules, and will bind polymers where multiple potential binding sites are presented. There are known examples of both inorganic and organic molecules which are recognized by antibodies.

Antibodies are frequently used as the affinity reagent in biosensors. The commonest isotype used is the immunoglobulin G (IgG) molecule, and though this sensing mechanism would work with the other subtypes, it is most likely that most applications will use IgG, as the majority of commercially available antibodies with defined target specificities are IgG molecules. Monoclonal antibodies with well-defined binding targets are typically IgG.

Antibodies are made of one or more protein chains. Each mammalian antibody contains two identical large "heavy" chains, and two identical copies of a "light chain". Though the general structure of all antibodies is very similar, a small region at the tip of the protein (the paratope) is extremely variable, allowing millions of antibodies with slightly different tip structures, or antigen binding sites, to exist. This region is known as the hypervariable region. Each of these variants can bind to a different target (antigen). This huge diversity of antibodies allows the immune system to recognize an equally wide diversity of antigens. Engineered antibody fragments can be also considered for the sensing mechanism, but for this application the fragment would have to be able to bind the antigen, and some types of antibody fragment may have lost this function.

The unique part of the antigen (analyte) recognized by an antibody is called an epitope. Epitopes bind with their antibody in a highly specific interaction, called induced fit, which allows antibodies to identify and bind only their unique antigen in the midst of the millions of different molecules that make up an organism. Hydrogen bonds, hydrophobic bonds, electrostatic forces, and van der Waals forces influence the binding between antigens and antibodies. Moreover, pH, temperature and solvent play an important role in the stability of the complex. These are all bonds of a weak, non-covalent nature, yet some associations between an antigen and an antibody can be quite strong. Accordingly, the affinity constant for antibody-antigen binding can span a wide range, extending from below $10^5$ mol$^{-1}$ to more than $10^{12}$ mol$^{-1}$. Apart from the affinity of an antibody for an antigen, the overall stability of an antibody-antigen complex is also determined by the valency of the antigen and antibody and the structural arrangement of their interacting parts (epitope and paratope).

Accurate affinity constants can only be determined for monoclonal antibodies. Monoclonal antibodies are genetically identical molecules recognising one single epitope on the antigen. With polyclonal antibodies, on the other hand, a broad distribution of affinities may contribute to an apparent affinity constant. The apparent affinity constant may also be caused by the fact that polyclonal antibodies can recognise more than one epitope on the same antigen. Since antibodies normally harbor more than one binding domain per molecule, multiple co-operative bindings can take place between polyclonal antibodies and their antigens. This effect is termed avidity. As monoclonal antibodies react with only one single epitope on the antigen, they are more vulnerable to the loss of epitope through chemical treatment of the antigen than polyclonal antibodies. This can be offset by pooling two or more monoclonal antibodies to the same antigen.

The lipid used to prepare small unilamellar liposomes could be (but is not limited to) dioleoyl phosphatidylcholine (DOPC). In some cases the process might be followed optically, in which case the DOPC will be doped with a small amount (typically 2%) of a fluorescent lipid probe such as NBD-PE (1,2-dioleoyl-sn-glycero-3-phosphoethanolamine-N-(7-nitro-2-1,3-benzoxadiazol-4-yl)).

To deposit the lipid on the surface of the nanowire, the liposome suspension is injected directly into a measuring chamber where one or more nanowires are present. And the current in the nanowire measured to ensure that the pH of the solution is stable. The lipid layer is then washed with a second solution at a different pH and the integrity of the lipid layer confirmed by demonstrating that the nanowire does not detect this change in pH.

The strips 701, 714, pads 702, 710 or regions 705, 708 may be made from a single continuous piece of absorbent material, or may be made from discrete pads joined together to form the strips, pads or regions (as long as the joins do not interfere with the flow of fluids in the device), the respective regions 705, 708 of the joined pads having first and second receptor species. The first and second strips 701, 714 may be made as separate strips which are joined together, or as one continuous piece of material. The first and second strips 701, 714 may not necessarily lie in the same plane, e.g. the second strip 714 may provide a cross flow through a vertical plane of the absorbent material of the first strip 701 (not shown).

Figure 9:
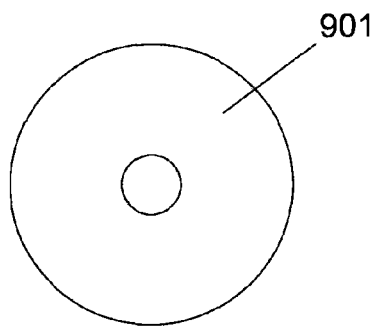
FIG. 9 illustrates schematically a computer readable media providing a program.

FIG. 9 illustrates schematically a computer/processor readable media 901 providing a computer program according to one embodiment. The computer program may comprise code for detecting the presence of an analyte using an apparatus, the apparatus comprising: a first and second receptor species, the first receptor species linked with a bound species and configured to interact with an analyte to form a first intermediate complex, the bound species for causing increased porosity of a membrane of an in-contact analyte sensor apparatus to correspondingly increase exposure of a sensing element of the analyte sensor apparatus to allow for production of a detectable electrical signal which can be used to sense the presence of the analyte, the second receptor species for interacting with the first intermediate complex to form a second intermediate complex; and a cleaving species, the cleaving species configured to interact with the second intermediate complex to release the bound species for use in sensing the presence of the analyte, the computer program comprising code to detect an electrical signal produced from the apparatus to detect the presence of the analyte.

In this example, the computer/processor readable media is a disc such as a digital versatile disc (DVD) or a compact disc (CD). In other embodiments, the computer readable media may be any media that has been programmed in such a way as to carry out an inventive function. The readable media may be a removable memory device such as a memory stick or memory card (SD, mini SD or micro SD).

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus for the selective release of a bound species based on the presence of an analyte, the apparatus comprising:
   a first and second receptor species located at first and second respective regions of a first piece of absorbent material,
      the first receptor species linked with a bound species and configured to interact with an analyte to form a first intermediate complex, the bound species for causing increased porosity of a membrane of an in-contact analyte sensor apparatus to correspondingly increase exposure of a sensing element of the analyte sensor apparatus to allow for production of a detectable electrical signal which can be used to sense the presence of the analyte, the second receptor species for interacting with the first intermediate complex to form a second intermediate complex; and a cleaving species, the cleaving species configured to interact with the second intermediate complex to release the bound species for use in sensing the presence of the analyte.

2. The apparatus of claim 1, wherein the first piece of absorbent material is configured to allow liquid to flow through the first piece of absorbent material by capillary action.

3. The apparatus of claim 1, wherein the first piece of absorbent material is configured to allow a first liquid to flow consecutively through the first and second regions.

4. The apparatus of claim 2, wherein the first liquid comprises the analyte, the flow of first liquid through the first region configured to allow the analyte to interact with the first receptor species to form the first intermediate complex.

5. The apparatus of claim 2, wherein the flow of first liquid through the second region is configured to allow the first intermediate complex to interact with the second receptor species to form the second intermediate complex.

6. The apparatus of claim 1, the apparatus comprising a second piece of absorbent material, the second piece of absorbent material connected to the first piece of absorbent material at the second region to allow a flow of second liquid through the second region.

7. The apparatus of claim 5, wherein the second liquid comprises the cleaving species, the flow of second liquid configured to allow the cleaving species to interact with the second intermediate complex to release the bound species.

8. The apparatus of claim 6, wherein the second liquid is configured to transfer the bound species from the first piece of absorbent material to the second piece of absorbent material after the bound species has been released.

9. The apparatus of claim 1, wherein the first and second receptor species are capable of interacting specifically with the analyte.

10. The apparatus of claim 1, the apparatus comprising an analyte sensor apparatus, the analyte sensor apparatus comprising a sensing element, the external surface of which comprises a membrane to inhibit exposure of the sensing element.

11. The apparatus of claim 5, the apparatus comprising an analyte sensor apparatus, the analyte sensor apparatus comprising a sensing element, the external surface of which comprises a membrane to inhibit exposure of the sensing element, the analyte sensor apparatus connected to the second piece of absorbent material to allow the bound species to interact with the analyte sensor apparatus to cause increased porosity of the membrane.

12. The apparatus of claim 1, wherein the apparatus comprises a fluid medium, the fluid medium comprising a charged species configured to provide an ionic gradient across the membrane.

13. The apparatus of claim 1, wherein the apparatus comprises a fluid medium, the fluid medium comprising a charged species configured to produce a detectable electrical signal when in contact with the sensing element.

14. The apparatus of claim 12, wherein the membrane is configured to be impervious to the charged species comprised in the fluid medium, the increased porosity of the membrane caused by release of the bound species allowing the charged species to diffuse through the created pores in the membrane from the fluid medium to cause a change in charge concentration at the exposed surface of the sensing element.

15. The apparatus of claim 14, wherein the charged species comprises positively or negatively charged ions such that diffusion of the ions through the membrane from the fluid medium causes a change in pH at the external surface of the sensing element.

16. The apparatus of claim 13, the apparatus further comprising source and drain electrodes, the source and drain electrodes electrically connected to the sensing element such that an electrical current may flow from the source electrode through the sensing element to the drain electrode when a potential difference is applied across the source and drain electrodes.

17. The apparatus of claim 16, wherein the apparatus is configured such that electrical connectors are electrically connected to the source and drain electrodes to apply the potential difference.

18. The apparatus of claim 17, wherein the apparatus is configured such that the electrical connectors are removably connected to the source and drain electrodes.

19. The apparatus of claim 16, wherein the apparatus is configured such that the source and drain electrodes are electrically insulated from the fluid medium.

20. The apparatus of claim 13, wherein the apparatus is configured such that the conductance of the sensing element varies with charge concentration at the external surface of the sensing element.

21. The apparatus of claim 10, wherein the apparatus forms part of a field-effect transistor.

22. The apparatus of claim 10, wherein the apparatus comprises a chamber for housing the analyte sensor apparatus.

23. A portable electronic device comprising a chamber for the apparatus of claim 1.

* * * * *